United States Patent [19]

Fiato et al.

[11] Patent Number: 5,140,049
[45] Date of Patent: Aug. 18, 1992

[54] METHOD FOR PRODUCING OLEFINS FROM $H_2$ AND $CO_2$ USING AN IRON CARBIDE BASED CATALYST

[75] Inventors: Rocco A. Fiato, Basking Ridge; Stuart L. Soled, Pittstown; Gary W. Rice, Scotch Plains; Sabato Miseo, Pittstown, all of N.J.

[73] Assignee: Exxon Research and Engineering Co., Florham Park, N.J.

[21] Appl. No.: 698,232

[22] Filed: May 6, 1991

Related U.S. Application Data

[63] Continuation-in-part of Ser. No. 427,668, Oct. 26, 1989, abandoned, which is a continuation-in-part of Ser. No. 289,277, Dec. 23, 1988, abandoned, which is a continuation of Ser. No. 59,106, Jun. 8, 1987, abandoned, which is a continuation of Ser. No. 791,442, Oct. 25, 1985, abandoned.

[51] Int. Cl.$^5$ .............................................. C07C 1/12
[52] U.S. Cl. ..................... 518/700; 518/713; 518/717; 518/719; 518/721
[58] Field of Search ............... 518/700, 713, 717, 719, 518/721

[56] References Cited

U.S. PATENT DOCUMENTS

| | | |
|---|---|---|
| 2,486,894 | 11/1949 | Watson . |
| 2,585,981 | 2/1952 | Watson . |
| 2,692,274 | 10/1954 | Kolbel et al. . |
| 4,279,830 | 7/1981 | Haag et al. . |
| 4,544,671 | 10/1985 | Soled et al. . |
| 4,544,674 | 10/1985 | Fiato et al. . |

FOREIGN PATENT DOCUMENTS 709560  5/1954  United Kingdom .

OTHER PUBLICATIONS

Storch et al, The Fischer-Tropsch and Related Synthesis, John Wiley, NY, 1951, pp. 241-243, 478-479, 491, 608.

Anderson, The Fischer-Tropsch Synthesis, Academic Press, New York, 1984, pp. 1, 9, 10, 21, 27.

Primary Examiner—Howard T. Mars
Attorney, Agent, or Firm—Estelle C. Bakun

[57] ABSTRACT

This invention relates to a process for producing $C_2$-$C_{20}$ olefins from a feed stream consisting of $H_2$ and $CO_2$ using an iron-carbide based catalyst.

20 Claims, No Drawings

METHOD FOR PRODUCING OLEFINS FROM $H_2$ AND $CO_2$ USING AN IRON CARBIDE BASED CATALYST

This application is a continuation-in-part of application Ser. No. 427,668, filed Oct. 26, 1989 now abandoned which is a Continuation-in-Part of U.S. Ser. No. 289,277 filed Dec. 23, 1988, which is a Rule 60 Continuation of U.S. Ser. No. 059,106, filed Jun. 8, 1987, which is a Rule 60 Continuation of U.S. Ser, No. 791,442, filed Oct. 25, 1985, all abandoned.

FIELD OF THE INVENTION

This invention relates to a process for producing olefins from hydrogen ($H_2$) and carbon dioxide ($CO_2$) by using an iron-carbide based catalyst.

BACKGROUND OF THE INVENTION

CO Hydrogenation

The increasing demand for energy has led to renewed interest in non-traditional sources of feedstocks. For instance, coal was used as a source for gaseous fuel ("town gas") during earlier parts of this century. Much work was done at that time to produce higher molecular weight hydrocarbons from the synthesis gas. That work, involving carbon monoxide (CO) hydrogenation chemistry, was revived by Germany during World War II and currently enjoys moderate use at the SASOL plants in South Africa.

Research continues on the $CO-H_2$ chemistry because of the potential for converting low value feedstocks into higher value products. Carbon dioxide ($CO_2$) is the major product of combustion processes and is available at relatively high pressure as a diluent in many gas fields throughout the world. However, relatively little attention has been paid to the conversion of $CO_2$ into hydrocarbons.

U.S. Pat. Nos. 4,544,671, Fiato et al, and 4,544,674, Soled et al, describe iron-carbide based catalyst used to convert a feed stream of CO and $H_2$ to olefins. U.S. Pat. No. 4,279,830, Haag et al, is also directed to a process for converting CO and $H_2$ to $C_3+$ products. Haag et al discloses a procedure for generating an iron-carbide based catalyst. However, the results obtained in these three cases did not show a product rich in $C_2$–$C_4$ olefins.

Frequently, $CO_2$ is produced when iron based catalysts are used in CO hydrogenation. The $CO_2$ is formed from the simultaneously occurring water gas shift reaction (WGS):

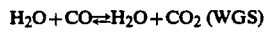

$$H_2O + CO \rightleftharpoons H_2O + CO_2 \text{ (WGS)}$$

where the water is formed as a by-product of the CO hydrogenation. The $CO_2$ formed in the WGS reaction can be suppressed by adding $CO_2$ to the feed stream following Le Chataliens principle. For example, U.S. Pat. Nos. 2,585,981, 2,486,894 and 2,486,895 are directed to the catalytic hydrogenation of CO with an iron-containing catalyst to produce hydrocarbons, oxygenated hydrocarbons and mixtures thereof. There, $CO_2$ was added to the reactant stream until the ratio of moles of hydrogen to moles of carbon dioxide and carbon monoxide is about 0.6. This causes the net production of $CO_2$ in the reaction zone to be substantially inhibited. In addition, the amount of $CO_2$ was regulated to result in minimal $CO_2$ production, with care taken not to convert the $CO_2$ to hydrocarbons.

U.K. Patent No. 709,560 is another example of CO hydrogenation where the presence of $CO_2$ acts to suppress the net formation of $CO_2$ produced by the water gas shift reaction. There is no disclosure or suggestion that $CO_2$ hydrogenation is taking place.

In the past, $CO_2$ was not looked to as a favorable component for the hydrogenation feed stream for a number of reasons. Carensbourg et al, Reviews in Inorganic Chemistry, Vol. 7, No. 4, p. 315–339 (1986), for instance, informs us that (i) hydrogenation of $CO_2$ was generally much more selective toward methane than CO which nearly always produces a significant amount of higher hydrocarbons and (ii) that the activation energy for the methanation of $CO_2$ was lower than that for CO, resulting in significant methane production from $CO_2$ at temperatures where CO methanation did not occur and, finally, (iii) that certain catalysts were more efficient at methanating $CO_2$ than CO, while the reverse was true for another group of catalysts.

$CO_2$ Hydrogenation

Anderson, The Fischer-Tropsch Synthesis, Academic Press, N.Y., (1984), and Dautzenberg et al, Reviews in Inorganic Chemistry, Vol. 7, No. 4, p. 315–339 (1986), show CO hydrogenation catalysts used to hydrogenate $CO_2$. The results indicate poor selectivity to olefin products in the $C_2$–$C_{20}$ range. In addition, it was concluded that as the $CO_2/H_2$ ratio was increased, the performance of the CO hydrogenation catalyst declined under conditions where CO hydrogenation normally would lead to higher hydrocarbon formation. Also, the CO hydrogenation catalyst was believed to produce high levels of undesirable methane. Anderson demonstrated the selectivity of a typical Fischer-Tropsch ruthenium on alumina catalyst, finding that methane was the primary product of $CO_2$ hydrogenation with only traces of $C_{2+}$ being formed. By contrast, the same catalyst produced significant amounts of $C_{2+}$ during CO hydrogenation under the same reaction conditions.

In Guerrero et al, React. Kinet. Catal. Lett., Vol. 3, No. 2, p. 349–354 (1986), the hydrogenation of $CO_2$ on activated carbon-supported iron catalysts was carried out at atmospheric pressure $H_2:CO_2$ ratio of 4:1. It was found that the using an specific activities for the reaction were lower than those obtained for CO hydrogenation using catalysts. It was also determined that CO and $CH_4$ are the only high yield products obtainable in the hydrogenation of $CO_2$ under the experimental conditions used.

Barrault et al, React. Kinet. Catal. Lett., Vol. 17(3–4) p. 373–378(1981), utilized a typical iron catalyst to explore the selective synthesis of hydrocarbons from the hydrogenation of $CO_2$. Comparison of the results of CO and $CO_2$ hydrogenation demonstrated: the reactivity of $CO_2$ is low compared to that of CO; the main product of the $CO_2$ reaction is CO; the selectivities to $CH_4$ and saturated hydrocarbons are higher for the ($CO_2$, $H_2$) reaction, but lighter hydrocarbon production, especially olefins, is lower. Berrault summized that the only hydrocarbons formed by $CO_2$ hydrogenation, except for methane, were formed only from the carbon monoxide produced and not directly from the carbon dioxide.

T. Wierzchowski, React. Kinet. Catal. Lett., Vol. 30, No. 2, 203–207(1986), studied the hydrogenation of $CO_2$ on three different series of catalysts, Fe/MgO, Ni/Ti, and Cr/Zn doped with potassium, finding that $CO_2$ is mainly converted to CO which is consecutively converted to $C_{2+}$ hydrocarbons and alcohols.

As can be seen, the catalytic hydrogenation of $CO_2$ to produce hydrocarbons of various types is known. However, much of the hydrocarbon made was in the form of methane. Barrault et al, React. Kinet. Catal. Lett., Vol. 17 (3-4), p. 373 (1981), discusses a process for producing hydrocarbons using iron-copper supported catalysts.

Similarly, U.S. Pat. No. 2,692,274 to Kolbel et al shows how various hydrocarbons may be produced by hydrogenating $CO_2$ using an oxidic iron based catalyst. Substantial amounts of methane were produced as a product of the hydrogenation.

Unlike the above references which hydrogenated $CO_2$ directly, Kolbel teaches a multistage recycle reactor system where substantial amounts of water are removed between stages. Kolbel is different from the above prior art and the repent invention where neither recycling nor water removal are employed.

The present invention directly hydrogenates $CO_2$ affording unexpectedly high amounts of $C_2$-$C_{20}$ olefins, whereas the direct hydrogenation of $CO_2$ was previously known to produce only CO and $CH_4$ as primary products. In addition, it is known that the removal of water causes WGS equilibrium to shift so that it favors the production of CO. The CO formed, as a result, undergoes hydrogenation. Only a relatively low percentage of the feed stream is converted in each stage. Therefore, Kolbel's process is not very efficient in converting $CO_2$ to desirable $C_{2+}$ olefin products, and requires several passes to accomplish the process.

In Solymosi et al, J. Chem. Soc. Faraday Trans. I, Vol. 77, p. 1003 (1981), the formation of methane from carbon dioxide using a ruthenium on alumina catalyst is shown.

The disclosure in Pijolat et al, CR. Acad. Sci. Paris, S.II, T295, p. 343 (1982) deals with the hydrogenation of carbon dioxide over iron-on-alumina catalysts. The selectivity of the reaction to methane appears to be greater than 30%. Less than 40% of the $C_2$ to $C_4$ fraction is olefinic. See the Table on page 344.

In He et al, ACS Div. Petri. Chem., St. Louis, April 1984, p. 332, a $ZrO_2$ catalyst is shown to produce variously methane, methanol, branched alkanes and aromatics when fed $CO_2$ and/or CO.

A general study of the activities and selectivities of silica-supported Co, Fe and Ru catalyst in hydrogenating $CO_2$ is found in Weatherbee et al, J. Catalysis, Vol. 87, p. 352 (1984). The catalysts produced very high levels of $C_1$ and very low levels of $C_{2+}$ products. The $C_{2+}$ olefin production was consequently low, although not specifically discussed.

The prior art has had little success in improving the conversion of $CO_2$ to higher molecular weight hydrocarbon products and even less success producing olefins in the $C_2$-$C_{20}$ range. The known prior art does not disclose the use of an ironcarbide based catalyst in the production of liquid hydrogenation products directly from a feed stream free of CO and consisting of $CO_2$ and $H_2$ reactants.

Therefore, it is an object of this invention to provide a novel method for producing $C_2$-$C_{20}$ olefins from a feed stream containing primarily $CO_2$ and $H_2$.

It is a further object of this invention to provide a method for preparing olefins by $CO_2$ hydrogenation while minimizing methane produced therein.

Still another object of this invention is to provide a method for producing olefins by passing a $CO_2$ and $H_2$ feed stream over an iron-carbide based catalyst.

Other objects of the invention will become apparent to those skilled in the art upon a reading of the following description to be taken in conjunction with the specific examples provided herein for illustrative purposes.

SUMMARY OF THE INVENTION

This is a nonrecirculating process for producing $C_2$-$C_{20}$ olefins from a gaseous mixture containing $H_2$ and $CO_2$. It is a catalytic process using an iron-carbide based catalyst. The catalyst may optionally contain other first row transition metal cocatalysts, preferably Cu, Co, Mn or Zn. Also, the catalyst may contain Cu, alkali or alkaline earth metal promoters such as potassium or sodium salts. The catalyst, depending upon the other cations present, is generally isostructural with $Fe_5C_2$ (Hagg carbide) or $Fe_3C$ (cementite) or a mixture of the two if the co-catalytic metal is easily carbided (e.g., Co) or the composition may contain separate phases of metal oxides if the co-catalytic metal is not easily carbiding (e.g., Mn, Zn) or, in some instances, separate phases of reduced metal may occur (e.g., Cu). However, the iron is always carbided in the catalyst composition. The BET surface area is generally greater than about 5 $m^2$/gm. The process may be operated in a slurry using the catalyst in a liquid solvent or may be operated as a fixed bed.

DESCRIPTION OF THE PREFERRED EMBODIMENTS

As noted above, this process is one for producing $C_2$ to $C_{20}$ olefins from $CO_2$ and $H_2$ directly by the use of an iron-carbide based catalyst and without the use of recirculation or water removal.

The catalyst used in this process is generically one containing an iron carbide at least a portion of which is isostructural with $Fe_5C_2$ (Hagg carbide) or $Fe_3C$ (cementite) or mixture thereof. It may be finely divided and generally will have a BET surface area of greater than about 5 $m^2$/g. The larger the specific surface area, the better is the reaction rate; consequently, specific surface areas of greater than 50 $m^2$/g are desired and greater than about 100 $m^2$/g are preferred. The total carbon content of the catalyst is less than 80% by weight, and preferably greater than about 5% by weight. Some inclusions of the $\beta$ and $\gamma$ form of elemental iron are permissible but should be kept to a minimum. The amount of iron oxide, whether it be in a separate included phase, or found on the surface of the catalyst should be kept to a minimum. The catalyst is both less selective for olefinic hydrocarbons and less active in hydrogenating $CO_2$ when the oxide is present.

Above, the catalyst was described as being at least part isostructural with at least one of the two iron carbides $Fe_3C$ and $Fe_2C_5$. Other Periodic Table first row transition metals, i.e., Sc, Ti, V, Cr, Mn, Fe, Co, Ni, Cu and Zn, may be included in the catalyst. Particularly preferred metals are one or more of Mn, Co, Cu or Zn. The form of the first row transition metal in the composition varies depending upon the metal. The iron must be in the form discussed above. The other metals may be in various forms depending largely upon the method of preparing the composition used and the identity of the co-catalyst metal. For instance, metals which are easily carbided will typically be found in solid solution with the iron carbide matrix discussed. Other less-easily-carbided metals, such as Mn or Zn, may be found in separate and/or metastable oxide phases in the iron carbide matrix. These materials are especially reactive in hydrogenating $CO_2$. Some co-catalyst metals, such as Cu, may exist in the iron carbide matrix as separate elemental metal phases.

The catalysts may be made by several different methods. One such method for making compositions suitable as catalysts for this process may be found in U.S. Pat. No. 4,518,707, to Soled and Fiato, issued May 21, 1985; the entirety of which is incorporated by reference. That patent teaches the production of iron-cobalt-carbides through a spinel-to-carbide synthesis route. Although the disclosure therein is limited to Co-type feed stream mixtures reacted with iron and cobalt, the process may also be used to produce carbides containing other first row transition metals.

By the term "spinel" is meant a crystal structure whose general stoichiometry corresponds to $AB_2O_4$, where A and B can be the same or different cations. Included within this definition is the commonly found spinel, $MgAl_2O_4$. A and B can have the following cationic charge combinations: $A=+2$, $B=+3$, $A=+4$, $B=+2$, or $A=+6$, $B=+1$. Spinels contain an approximately cubic close-packed arrangement of oxygen atoms with a ⅛th of the available tetrahedral interstices and ½ of the octahedral interstices filled, and can exhibit hundreds of different phases. Further description of the spinel structure can be found in Structural Inorganic Chemistry by A. F. Wells, Third Edition, Oxford Press, and the article Crystal Chemistry and Some Magnetic Properties of Mixed Metal Oxides with the Spinel Structure by G. Blasse, Phillips Research Review Supplement, Volume 3, p. 1–30, (1964). By the term "isostructural" is meant crystallizing in the same general structure type in that the arrangement of the atoms remains very similar with only minor changes in unit cell constants, bond energies, and angles. By the term "single spinel phase" is meant one structural and compositional formula, corresponding to a single spinel material into which all of the metal components are incorporated, and exhibiting one characteristic X-ray diffraction pattern.

A high surface area spinel composition can be made by a process in which an acidic aqueous solution of one or more first row transition metals and iron salts of an alpha-hydroxy aliphatic carboxylic acid, is evaporated to dryness, leaving an amorphous residue, which is then heated at elevated temperature to form substantially the spinel, in a single spinel phase, being isostructural with $Fe_3O_4$ and possessing a surface area greater than 5 $m^2$/g, preferably above 50 $m^2$/g. The heating is conducted such that no significant loss in surface area of the final spinel is incurred.

The synthesis of the spinels involves the use of the organic, saturated, aliphatic, alphahydroxy carboxylic acid to form a complex salt, which is soluble in the aforementioned aqueous medium, at a pH on the acidic side, i.e., pH of 5–7.

The method utilizes an alpha-hydroxy aliphatic carboxylic acid which acts as a solubilizing agent for the iron and cobalt salts in the aqueous solution. Any saturated aliphatic alpha-hydroxy carboxylic acid, containing at least one alpha-hydroxy grouping, can be used to form the soluble iron and first row transition metal salts in the subject invention process in mildly acidic aqueous solution, is considered to be within the scope of this invention. Representative examples of such acids which can be mono-hydroxy or di-hydroxy or mono-carboxylic or di-carboxylic are glycolic, malic, glyceric, mandelic, tartaric, lactic acid and mixtures thereof. A preferred carboxylic acid used in the process is glycolic acid.

The amount of acid used is at least the stoichiometric amount, i.e., 1 to 1 molar ratio for each metal present and preferably in about a 5–10% molar excess of the stoichiometric amount. Higher ratios can be used, if it is economical to do so. Lower amounts can also be used but often result in incomplete iron and first row transition metal acid salt formation.

The first step in the process comprises forming an aqueous solution by dissolving iron salts and first row transition metal salts, in a watersoluble salt form such as their nitrates, sulfates, chlorides, acetates, and the like, in water.

The concentration of the salts in the aqueous liquid is not critical to the extent that the salts are present in less than a saturated solution to avoid precipitation. For example an 80–90% saturated solution, of combined dissolved metal molarities for avoiding precipitation in the process, can be effectively used.

The temperature of the aqueous solution is not critical and may be above room temperature to aid in the solubilizing process. However, room temperature is adequate and is the temperature generally used in the process. The pressure also is not critical in the process and atmospheric pressure is generally used.

The aqueous solution can also contain a small amount of organic solvent such as ethanol, acetone, and the like for aiding in the solubilizing of the iron and cobalt salts of the alpha-hydroxy carboxylic acid.

Following the dissolving of the iron and first row transition metal salts, the alpha-hydroxy carboxylic acid is added, together with a sufficient quantity of base, usually being ammonium hydroxide, sodium hydroxide, potassium hydroxide, and the like, preferably ammonium hydroxide, to solubilize the resulting acid salts. The amount of base added is sufficient to keep the pH in the range of about 5 to 7.0.

It should be noted that the exact sequence of steps need not be adhered to as described above, with the proviso that the resulting aqueous solution contain dissolved metal salts in stoichiometric amounts as iron and first row transition metal salts of alpha-hydroxy carboxylic acid in solution. If there are any insoluble materials present after addition of the base and organic acid, they should be filtered prior to the evaporation step.

At this point, the resulting solution is evaporated, as for example, by air drying, or under reduced pressure, at elevated temperature, as practiced in a rotary evaporator, or in a vacuum drying oven.

The resulting material from the evaporation step is an amorphous residue, generally being a powder or glass. This residue is heated at elevated temperature at 100° to 600° C. for about 1 to 24 hours in generally air to result in a substantially single spinel phase which is isostructural with $Fe_3O_4$, as determined by X-ray diffractometry, as previously described herein. Preferred temperature range is 100°–400° C., and particularly preferred is about 350° C. for single spinel phase formation.

A metallic iron-first row transition metal material can be produced by reducing the above-described iron-cobalt spinel in a reducing atmosphere at elevated temperature generally of about 240° C. and above and preferably 300° to 400° C. The reduction can be carried out with various reducing gases including hydrogen, $H_2$/CO, and the like, and mixtures thereof. Preferably hydrogen gas alone is generally used in an inert carrier medium such as helium, neon, argon, or nitrogen, in the absence of CO when substantially pure, non-carbided alloy is desired.

The alloy can be prepared ex situ in a tube reactor or in situ in the slurry reactor. The in situ preparation is conducted in the slurry apparatus when the above-described spinel is reduced while suspended in the slurry liquid, in a reducing atmosphere (preferably containing hydrogen) at elevated temperature of about 240° C., or above, preferably at 240°–300° C, and at a space velocity, pressure, and hydrogen concentration sufficient to cause substantial reduction of the spinel to the alloy. Substantial reduction is complete when the X-ray diffraction pattern shows a pattern substantially isostructural with alpha-iron.

The carbided iron-first row transition metal alloy, having an X-ray diffraction pattern isostructural with $Fe_5C_2$, can be produced by carbiding the iron-first row transition metal alloy, described hereinabove, in a suitable carbiding atmosphere at elevated temperature of up to about 400° C. Temperatures above 500° C. lead to formation of Fe carbides which are isostructural with $Fe_3C$, cementite. Other phases, as discussed above, may be present at this point.

Carbiding atmospheres which can be used to produce the subject reduced, carbided, catalyst include CO, $CO/H_2$, aliphatic hydrocarbons, aromatic hydrocarbons, and the like. A preferred carbiding atmosphere is $CO/H_2$. When using $CO/H_2$ carbiding atmosphere, mixtures of $CO/H_2$ can be used in a 1:10 to 10:1 molar ratio. A preferred molar ratio used for carbiding purposes is 1:1.

The carbiding step is generally conducted at a temperature of about 250° C., or above and preferably at 260° C. to 300° C. A preferred method of carbiding the alloy is in situ in the slurry liquid to be used in the process. A particularly preferred method is where the spinel is treated with a mixture of $CO/H_2$ and reduced and carbided in situ in one step prior to hydrocarbon synthesis. The pressure is generally about 1–5 atmosphere, and a space velocity of about 20–20,000 v/v/hr is chosen in order to completely carbide the starting iron oxide which can be determined by X-ray diffractometry when the material becomes isostructural with Haag carbide, $Fe_5C_2$.

The resulting composition is an active slurry catalyst for producing $C_2$–$C_{20}$ olefins in the described $CO_2$ hydrogenation slurry process.

Another suitable composition can be produced using the processes disclosed in U.S. Pat. Nos. 4,607,020 to Soled and 4,584,323 to Fiato, the entirety of which are incorporated by reference. Therein are disclosed catalysts which are made by a portion of the synthesis process described above but which processes include the step of impregnating or otherwise adding a potassium-containing and a copper-containing material to the iron spinel noted above. The amount of copper promoter employed will range from about 0.1 to 5 gram atom percent based on the combined iron and cobalt content of the spinel preferably the amount of copper promoter will range from about 0.5 to 2 gram atom %. The copper may be deposited on or added to the spinel by impregnating the spinel with a solution of a suitable copper salt such as copper nitrate, sulfate, halide, acetate, etc.

The potassium-copper promoted spinels undergo unexpectedly facile in-situ reduction in a slurry liquid and pretreatment to form potassium-copper promoted iron-cobalt alloys, which are further in situ carbided to form active slurry catalysts in a slurry process for making $C_2$–$C_{20}$ olefins from $CO_2/H_2$.

The potassium-copper promoted iron-cobalt alloy can be produced by reducing the above-described potassium-copper promoted iron-cobalt spinel in a reducing atmosphere at elevated temperature generally of about 240° C. and above and preferably 300° C. to 400 C. The reduction can be carried out with various reducing gases including hydrogen, $H_2/CO$, and the like, and mixtures thereof. Preferably hydrogen gas alone is generally used in an inert carrier medium such as helium, neon, argon, or nitrogen, in the absence of CO when substantially pure, non-carbided alloy is desired.

The alloy can be prepared ex situ in a tube reactor or in situ. The in situ preparation is conducted in the slurry apparatus when the above-described copper-promoted spinel is reduced while suspended in the slurry liquid, in a reducing atmosphere being preferably a hydrogen atmosphere at elevated temperature of about 240° C., or above, or preferably at 240°–300° C., at a space velocity, pressure, and hydrogen concentration sufficient to cause substantial reduction of the spinel to the alloy. Substantial reduction is complete when the X-ray diffraction pattern shows a pattern substantially isostructural with alpha-iron.

The above-described alloy is useful in forming a carbided, potassium-copper promoted iron-cobalt catalyst useful in the subject slurry process for making $C_2$–$C_{20}$ olefins.

Also, the above-described alloys and carbides, can be prepared independently of the slurry apparatus and may be pyrophoric and inconvenient to handle. In that case, the material may be passivated for a sufficient time to reduce or eliminate the pyrophoric tendency. Generally, the air or $O_2$ used in the passivating process is used in an inert gas stream carrier such as helium for a sufficient time to cause passivation. Generally, this is conduced preferably at room temperature, at a pressure and space velocity which are convenient and easy to control and to maximize the efficiency of the process needed for complete passivation.

A promoter agent can also be used in the composition and can be used to particularly promote olefin formation, for example, in the process. General classes of suitable promoter agents include hydroxides carbonates, bicarbonates, organic acid salts, e.g., acetates, inorganic acid salts, e.g., nitrates, halides, sulfates, of Group IA and IB and IIA and IIB metals including lithium, sodium, potassium, rubidium, cesium, barium, calcium, strontium, magnesium, copper, zinc, and the like. These promoters can be added to the catalyst or its precursors, if desired, simply by impregnating the catalyst or its precursors with an aqueous solution of one or more of said promoter agents and drying the resulting impregnate.

Representative examples of specific promoter agents are potassium carbonate, potassium sulfate, potassium bicarbonate, cesium chloride, rubidium nitrate, lithium acetate, potassium hydroxide, and the like. Preferred are the Group IA compounds and a particularly preferred promoter agent is potassium carbonate.

The promoter, if used, is generally present in about a 0.1 to 10 gram-atom % of metal ion based on the total combined metals gram-atoms. A preferred level of promoter agent is in the range of 1 to 2 gram-atom %. A particularly preferred spinel composition of the subject invention is $Fe_{2.85}$-(first row transition metal)$_{0.15}O_4$/2% K as potassium carbonate. In the empirical formulas used herein, the amount of the promoter agent, e.g., potassium, is expressed in terms of gram atom percent based on the total gram-atoms of metals used. Thus, "1 gram-atom percent of potassium" signifies the presence of 1 gram-atom of potassium per 100 total gram atoms of combined gram atoms of Fe and first row transition metal.

The process for producing $C_2$-$C_{20}$ olefins using an iron-carbide based catalyst, desirably produced in the manner described above, entails contacting of $CO_2$ and $H_2$ in the presence of the catalyst and recovering the products.

Although a fixed bed process can be used, a preferred contacting step for operating the $CO_2$ hydrogenation process is a slurry-type process wherein the catalyst is in fine particle size and has a high surface area being above 5 $m^2$/g. The catalyst is suspended in a liquid hydrocarbon and the $CO_2$/$H_2$ mixture forced through the catalyst slurry allowing good contact between the $CO_2$/$H_2$ and the catalyst to initiate and to maintain the hydrocarbon synthesis process.

Advantages of a slurry process over that of a fixed bed process are better control during the reaction and that better control over catalyst activity maintenance by allowing continuous recovery and rejuvenation procedures to be implemented. The slurry process may be operated in a batch or in a continuous cycle mode. In the continuous cycle mode, the entire slurry phase (catalyst and liquid) may be circulated in the system allowing for better control of the primary products residence time in the reaction zone.

The slurry liquid used in the process is a liquid at the reaction temperature, must be substantially chemically inert under the reaction conditions and must be a relatively good solvent for $CO_2$/$H_2$ and possess good slurrying and dispersing properties for the finely divided catalyst. Representative classes of organic liquids which may be utilized are high boiling paraffins, aromatic hydrocarbons, ethers, amines or mixtures thereof. The high boiling paraffins include $C_{10}$-$C_{50}$ linear or branched paraffinic hydrocarbons; the aromatic hydrocarbons include $C_2$-$C_{20}$ alkyl substituted single ring and multi- and fused ring aromatic hydrocarbon; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. The slurry liquid may contain N and O in the molecular structure but not S, P, As or Sb, since these are poisonous to the slurry process. Representative examples of specific liquid slurry solvents useful are dodecane, tetradecane, hexadecane, octadecane, cosane, tetracosane, octacosane, dotriacontane, hexatriacontane, tetracontane, tetratetracontane, toluene, o-, m-, and p-xylene, mesitylene, $C_1$-$C_{12}$ mono- and multi-alkyl substituted benzenes, dodecylbenzene, naphthalene, anthracene, biphenyl, diphenylether, dodecylamine, dinonylamine, trioctylamine, and the like. Preferred liquid hydrocarbon slurry solvents are octacosane or hexadecane, or isoparaffins with 16 or more carbon atoms.

The amount of catalyst used in the liquid hydrocarbon slurry solvent is generally about 10 to 60 g of dry catalyst per 500 g slurry liquid. Preferably about 30 to 50 g dry catalyst per 500 g slurry liquid slurry is utilized, being in about a respective 5:1 to 10:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases. In a typical laboratory unit the rate of stirring is generally carried out in the range of about 600 to 1,200 rpm and preferably 1,000 to 1,200 rpm.

Prior to the hydrocarbon synthesis run, the reduced and carbided catalyst may be conditioned in the apparatus by purging with nitrogen to remove reactive oxygen-containing gases and then the temperature is increased while stirring to the reaction temperature range. Then the system is generally subjected to a hydrogen treatment for a sufficient time to insure complete removal of any surface iron oxide present which would interfere in hydrocarbon synthesis.

Optionally, and preferably if the catalyst is prepared in situ, then the hydrogen treatment is generally not required or is only practiced for a short period of time. The pressure and space velocity during the inert gas-hydrogen conditioning step are not critical and can be utilized in the range which is actually used during actual hydrocarbon synthesis reactions.

Following the conditioning step, the $CO_2$/$H_2$ feedstream is introduced into the slurry catalyst chamber and the pressure, space velocity temperature, and $H_2$/$CO_2$ molar ratio is then adjusted, as desired, for hydrocarbon synthesis conditions.

As noted above, the catalytic material may be used in a fixed bed or fluidized bed and, when so used, may be placed on known refractory supports such as alumina, silica, mullite, diatomaceous earth, silica-alumina comixtures or other materials known to provide stable supportive high surface area.

A magnetically stabilized bed as is described in U.S. Pat. No. 4,115,927 is also suitable for this reaction.

The operating conditions for this process are generally as found below:

|  | Fixed Bed | Slurry |
| --- | --- | --- |
| T (°C.) | 240–300 | 240–280 |
| (preferred) | 250–275 | 250–275 |
| Press. (psig) | 50–200 | 50–200 |
| (preferred) | 50–120 | 50–120 |
| $H_2$/$CO_2$ (molar ratio) | 0.5:1–9:1 | 0.5:1–9:1 |
| (preferred) | 5:1–8:1 | 5:1–8:1 |
| SHSV (volume fresh gas/ unit of catalyst/hr) | 100–10,000 | 100–10,000 |
| CSTR stir speed (rpm) | — | 600–4,000 |
| Diluent gases | $N_2$/Ar/$CH_4$/ light hydrocarbons | $N_2$/Ar/$CH_4$/ light hydrocarbons |

Generally speaking, high temperatures tend to produce lighter products and more methane. Low temperatures and high pressures tend to lead to heavier hydrocarbons even in the wax range.

The feedstock is preferably made up of $CO_2$ and $H_2$ only. Diluents such as noble gases (Ar, Ne, etc.), inert gases ($N_2$, etc.) may be present if kept at acceptable minimums.

The percent $CO_2$ conversion obtainable in the subject process, while providing substantial quantities of $C_2$-$C_{20}$ olefins, ranges from about 30 to 80 percent and usually about 50 to 60 percent for sufficient $C_2$-$C_{20}$ olefin production.

The term "total hydrocarbons" produced in the process is related to the selectivity or percent $CO_2$ conversion to hydrocarbons and alcohols being those hydrocarbons from $C_1$ to about $C_{40}$ inclusive.

The percent $C_2$-$C_{20}$ hydrocarbons of the total hydrocarbons produced including methane and above is about 60 to 90 wt. %. The percent of $C_2$-$C_{20}$ olefins produced, of the $C_2$-$C_{20}$ total hydrocarbons produced is about 60 to 70 wt. %. A large portion of the olefins produced in the process are alpha olefins.

The selectivity to methane based on the amount of $CO_2$ conversion is about 1 to 10 weight percent to total hydrocarbons, produced. Preferably about 5 percent, and lower, methane is produced in the process.

Preferably, the reaction process variables are adjusted to minimize methane production, maximize percent $CO_2$ conversion, and maximize percent $C_2$-$C_{20}$ olefin selectivity, while achieving activity maintenance in the catalyst system.

Having thus described the invention, the following are examples which illustrate the various workings of it. They are not intended to limit the invention in any way.

EXAMPLE 1

Carbide Catalyst Preparation

Preparation of $Fe_3O_4$ Spinel with 2%K Promoter 206 grams of ferric nitrate was dissolved in 150 cc of water. A second solution was prepared by mixing 41.6 grams of 85% glycolic acid with a sufficient quantity (~45 cc) of ammonium hydroxide such that the resulting pH of the ammonium glycolate solution was about 6.5. The ammonium glycolate solution constituted 0.51 moles of glycolic acid such that about a one to one molar ratio of iron to glycolic acid resulted. The ammonium glycolate solution was added to the aqueous solution containing iron and the contents stirred. The resulting solution was allowed to evaporate by air drying. Upon drying at room temperature the resulting solid was shown by X-ray diffraction to be an amorphous material because of lack of sharp discrete reflections. The solid was heated in air at 350° C. for 1 hour. An X-ray diffraction pattern of the resulting material showed it to be a single phase iron spinel ($Fe_3O_4$). The X-ray diffraction peaks were broadened relative to a compositionally equivalent material obtained by a high temperature procedure. This indicated that the resulting obtained material was of very small particle size. The surface area of the resulting material was about 86 square meters per gram. The resulting material was impregnated with two grams atomic percent of potassium using an aqueous solution of potassium carbonate and drying of the resulting impregnated sample at 110° C. The resulting solid had an empirical formula of $Fe_3O_4$/2%K.

Preparation of Ex Situ Carbide

The above oxide material was treated at 350° C. in a tubular reactor in a stream of 15 volume percent hydrogen/70% helium/15% CO at 60 v/v/hr for one hour. Following this the sample was cooled to room temperature and 2 volume % oxygen in helium was introduced for two hours to passivate the material. The X-ray diffraction pattern of the resulting material was isostructural with $Fe_5C_2$. The BET nitrogen surface area of the material was about 128 m$^2$/g. Analysis showed that about 60 weight percent of the material was carbon and thus the material was a composite of $Fe_5$/$C_2$/2%K and surface carbon. Since the calculated % carbon for $Fe_5C_2$ is 8% excess carbon amounting to 52% of the total sample is present.

EXAMPLE 2

Iron Cobalt Carbide Catalyst Preparation

Preparation of $Fe_{2.85}Co_{0.15}O_4$ Spinel with 2%K Promoter 198.04 grams of ferric nitrate in 144 cc of water and 7.5 grams of cobalt nitrate (in 8 cc of water) were mixed together. To this solution was added a solution of 41.6 grams of 85% glycolic acid containing 45 cc of ammonium hydroxide until the pH of the ammonium glycolate solution was about 6.5. The ammonium glycolate solution constituted 0.51 moles of glycolic acid. Therefore, about a one to one molar ratio of total metals including iron and cobalt to glycolic acid resulted. The ammonium glycolate solution was added to the aqueous solution containing iron and cobalt salts and the contents stirred. The resulting solution was allowed to evaporate by air drying at room temperature. The resulting solid was shown by X-ray diffraction to be an amorphous material because of lack of sharp discrete reflections. The solid was heated in air at 350° C. for 2 hours. An X-ray diffraction pattern of the resulting material showed it to be a single (cobalt-iron) spinel phase isomorphous with $Fe_3O_4$. The X-ray diffraction peaks were broadened relative to a compositionally equivalent material obtained by a high temperature procedure. This indicated that the resulting obtained material was of very small particle size. The surface area of the resulting material was about 200 square meters per gram. Carbon analysis of the material indicated approximately a 0.15% carbon content. The resulting material was impregnated with two grams atomic percent of potassium using an aqueous solution of potassium sulfate and aqueous copper nitrate with one gram atom percent copper. The resulting impregnated sample was dried at 125° C. The solid was found to have the empirical formula $Fe_{2.85}Co_{0.15}O_4$/2% K/1% Cu.

Preparation of Alloy

The oxide obtained above was reduced at 400° C. in a stream of 15 volume percent hydrogen and 85 volume percent helium at 200 v/v/hr (SHSV) for 4 hours. One volume percent oxygen in helium was introduced at room temperature for one hour to passivate the material. The X-ray of the resulting material was isostructural with alpha iron. The resulting BET nitrogen surface area was 8m$^2$/g.

Preparation of Carbide

The above reduced material was treated at 400° C. in a stream of 15 volume percent hydrogen/80% helium/5% CO at 200 v/v/hr for four hours in a tube furnace. Following this, the sample was cooled to room temperature and 10 volume percent oxygen in helium was introduced for one hour to passivate the material. X-ray diffraction pattern of the resulting material was isostructural with $Fe_5C_2$. The BET nitrogen surface area of the material was about 118 m$^2$/g. Analysis showed that about 60–70 weight percent of the material was carbon. The material was a composite of $Fe_{4.75}Co_{0.25}C_2$/2 gram-atom % K, 1 gram-atom % Cu and surface carbon.

EXAMPLE 3

Reactor Pressure

The catalyst prepared in Example 1 was tested to determine the effect of reaction pressure upon the products of the reaction. The reaction conditions and results are shown in the Table below.

TABLE

| Pressure (psig) | 75 | 100 |
|---|---|---|
| % $CO_2$ Conversion | 36.6 | 38.1 |
| Selectivity (based on $C_1^+$ products - % Wt.): | | |
| % $CH_4$ | 16.5 | 10.8 |
| % $C_2^+$ | 83.5 | 89.2 |
| % olefins in $C_2$-$C_4$ | 80.0 | 95.5 |

Catalyst: $Fe_5C_2$/2% K as prepared in Example 1 contains greater than 50% total matrix carbon in the catalyst matrix.

Conditions: 270° C., 3800 v/g Fe/hr, 75 psig, $H_2$/$CO_2$ 7/1, octo-cosane solvent, Parr continuous stirred tank reactor, feed gas contained $H_2$, $CO_2$ and 36% $N_2$ as an internal standard.

The example demonstrates the applicability of the process over a range of pressure but also shows very good selectivity at higher pressures.

EXAMPLE 4

Higher Molecular Weight Products

The higher molecular weight products found in the stream produced in Example 3 (75 psig) were analyzed for type distribution. The results are shown in the Table below.

TABLE

| $C_{10}$ Product Distribution | (% Wt.) |
|---|---|
| α-olefin | 36.7 |
| β-olefin | 6.5 |
| n-paraffin | 13.3 |
| n-alcohol | 14.2 |
| all else | 29.4 |

This shows that the process is suitable for producing liquid hydrocarbons containing more than 45% α-olefins/n-alcohols in the $C_{10}$ fraction.

COMPARATIVE EXAMPLE 5

Selectivity

First, a conventional (precipitated mixed metal Fe/Cu/K/Si) catalyst, produced by coprecipitation, was introduced to a continuously stirred tank reactor. The catalyst had a composition of 93/2/2/3 on a gram atom basis. Next, the catalyst prepared in Example 1 was introduced to a similar reactor. Both catalysts were reacted with a feed stream of $CO_2$ and $H_2$ to determine the effect upon $CO_2$ hydrogenation selectivity as a fraction of various $H_2$/$CO_2$ molar feed ratios. The reaction conditions and results for each catalyst are shown below:

Conditions: 260°-270° C., 3800 v/g Fe/Hr, 75 psig, 10 vol. percent catalyst in octacosane solvent, Parr continuous stirred tank reactor, feed gas contained $H_2$, $CO_2$ and 30-50 volume percent $N_2$ as an internal standard.

| Catalyst | Fe/Cu/K/Si (Prior Art) | $Fe_5C_2$/2% K With >50% Total Amorphous Carbon in the Catalyst Matrix | | |
|---|---|---|---|---|
| Feed $H_2$/$CO_2$ | 7.0 | 7.0 | 3.0 | 1.7 |
| % $CO_2$ Conversion | 21 | 37 | 23 | 13 |
| Selectivity (based on $C_1^+$) | | | | |
| $CH_4$ | 64 | 16.5 | 6.2 | 4.2 |
| $C_2^+$ | 36 | 83.5 | 93.8 | 95.8 |
| % Olefin in $C_2$-$C_4$ | 28 | 80 | 95 | 99 |

The results show that the selectivity of the comparative catalyst towards the production of methane is significantly higher and demonstrates that the present invention is highly selective in the production of $C_{2+}$ olefinic hydrocarbons over a wide range of molar ratios of $H_2$:$CO_2$ in the feed. Limited methane formation is therefore possible over a broad spectrum of feed stream compositions.

While it will be apparent that the embodiments of the invention herein disclosed are well calculated to fulfill the objects of the invention, it will be appreciated that the invention is susceptible to modification, variation and change without departing from the proper scope or fair meaning of the subjoined claims.

What is claimed is:

1. A slurry process for directly converting $CO_2$ to $C_2$-$C_{20}$ comprising contacting a feed stream containing $CO_2$ and $H_2$ and substantially free of CO, with a slurry catalyst selected from iron base carbided catalysts having a crystal structure isostructural with $Fe_5C_2$, $Fe_3C$ and mixtures thereof, wherein the contacting is conducted at elevated temperatures and pressures and in a single pass, for a time sufficient to produce and recover $C_2$-$C_{20}$ olefins.

2. The process of claim 1 wherein the contacting is conducted in a temperature range from about 220° C. to about 280° C.

3. The process of claim 2 wherein the contacting is conducted in a pressure range from about 50 to about 120 psig.

4. The process of claim 4 wherein the feed stream has a molar ratio of $H_2$:$CO_2$ ranging from about 0.5:1 to about 20:1.

5. The process of claim 4 wherein the feed stream molar ratio of $H_2$:$CO_2$ ranges from about 5:1 to about 18:1.

6. The process of claim 1 wherein the catalyst additionally contains at least one promoter selected from alkali and alkaline earth metals.

7. The process of claim 6 wherein the promoter is potassium.

8. The process of claim 6 wherein the promoter is magnesium.

9. The process of claim 1 wherein the catalyst contains a first row transition metal selected from the group of manganese, copper and zinc.

10. The process of claim 9 wherein the first row transition metal is manganese.

11. The process of claim 9 wherein the first row transition metal is copper.

12. The process of claim 9 wherein the first row transition metal is zinc.

13. The process of claim 6 wherein the catalyst contains a first row transition metal selected from the group of manganese, copper and zinc.

14. The process of claim 13 wherein the first row transition metal is manganese.

15. The process of claim 13 wherein the first row transition metal is copper.

16. The process of claim 13 wherein the first row transition metal is zinc.

17. A process for directly producing $C_2$–$C_{20}$ olefins in a single pass from a feed stream consisting essentially of $CO_2$ and $H_2$ comprising the steps of contacting the feed stream with cobalt, potassium and an iron-carbide based slurry catalyst having a crystal structure isostructural with $Fe_2C_5$ and $Fe_3C$, in a continuously stirred tank reactor in a temperature range from about 240° C. to about 280° C. and a pressure ranging from about 50 psig to about 120 psig for greater than 24 hours, wherein the molar ratio of $H_2$ to $CO_2$ in the feed stream ranges from about 0.5:1 to about 9:1.

18. The process of claim 17 wherein the temperature ranges from about 250° C. to about 275° C.

19. The process of claim 17 wherein the pressure is 75 psig.

20. The process of claim 17 wherein the catalyst additionally contains copper.

* * * * *